United States Patent [19]

Sipin

[11] 3,953,152
[45] Apr. 27, 1976

[54] REGULATED FLUID PUMP

[76] Inventor: Anatole J. Sipin, 221 E. 78th St., New York, N.Y. 10021

[22] Filed: Aug. 2, 1973

[21] Appl. No.: 385,081

[52] U.S. Cl. ................................. 417/45; 417/411
[51] Int. Cl.² ........................................ F04B 49/06
[58] Field of Search ..................... 417/411, 45, 42; 318/139, 246

[56] References Cited
UNITED STATES PATENTS

| | | | |
|---|---|---|---|
| 3,410,059 | 11/1968 | Garnier | 318/139 X |
| 3,439,622 | 4/1969 | Welty et al. | 417/45 |
| 3,501,899 | 3/1970 | Allen | 417/45 X |
| 3,502,026 | 3/1970 | Toyoda | 417/45 X |

Primary Examiner—William L. Freeh
Assistant Examiner—G. P. LaPointe
Attorney, Agent, or Firm—Eric P. Schellin; H. K. Saalbach

[57] ABSTRACT

A system for the linear control and calibration of the flow of fluid through a pump in which the pump has a linear flow rate-to-fluid propeller speed relationship over a range of flow rates. A DC motor driving the fluid propeller has a linear drive speed-to-armature voltage relationship over a corresponding range of drive speeds. The voltage applied to the armature is regulated DC, the value of which provides an indication of the fluid flow rate. The system has particular utility in portable air pollutant measuring applications where a measured volume of air is pumped through a filter tube filled with a porous solid sorbent which is later subjected to chemical analysis.

30 Claims, 6 Drawing Figures

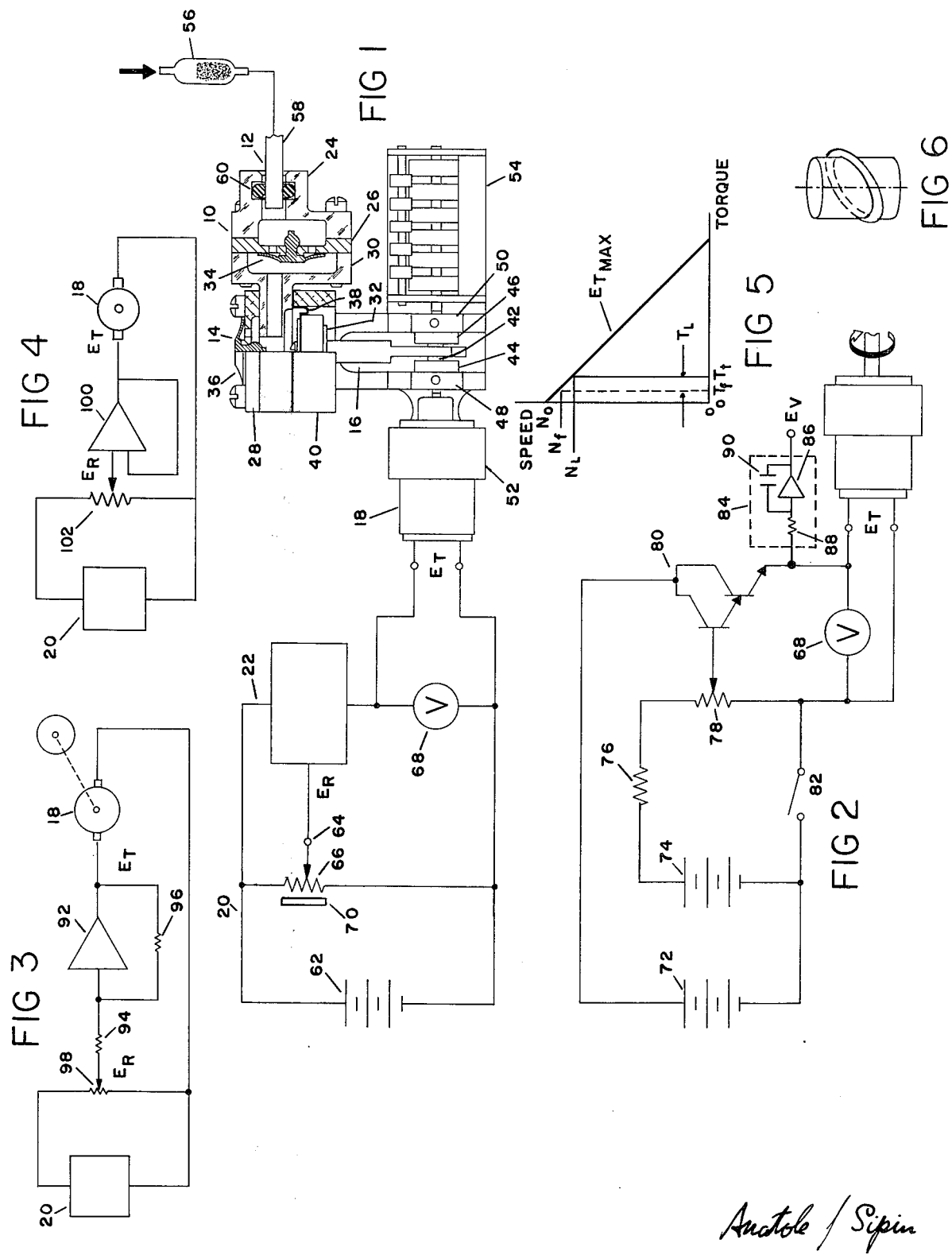

REGULATED FLUID PUMP

This invention relates to an improved regulated fluid pump, with a linear calibration.

Recent health regulations contain provisions for the establishment of standards for safe concentrations of toxic materials to which employees may be exposed. Employers are required to maintain the levels of pollutants below the standard limits and to assure the maintenance of safe levels by monitoring.

A method has been developed for measuring concentrations of pollutants in the environmental air by passing a measured volume of air through a filter tube filled with a porous solid sorbent, which is subsequently subjected to chemical analysis. To determine the concentration two quantities are required, the amount of pollutant removed by the sorbent and the total volume of air passed through the sorbent. Present specifications of the National Institute for Occupational Safety and Health and the U.S. Department of Labor require that the total volume of air sampled be within ± 5% accuracy, and that the selected air flow rate does not change more than 10% over a continuous four-hour period of operation. Representative of a sorbent-filled filter tube is one currently in use that is filled with 100 milligrams of 20/40 mesh activated charcoal for the collection of samples of organic vapors.

To adequately determine the concentrations of pollutants to which an employee is exposed, a weighted average of the pollutants in the air which is actually breathed is required. It is necessary, therefore, that a charcoal tube (for example) be carried by the employee for the duration of a work period, normally four or eight hours, and that air be passed through the tube at a constant flow rate during this period. The pollutant-collecting charcoal can be saturated after it has been exposed to an air sample with a total volume of 10 to 12 liters. To obtain a weighted average sample over a period of four or eight hours, a low and constant air flow rate is required; 40 to 50 cc/min for four hours of operation, 20 to 25 cc/min for eight hours of operation.

Existing battery-operated portable air pumps are of the piston type, and they are inefficient, causing the pumps to be relatively large and heavy if continuous operation for as long as 8 hours is required. Typically such pumps are operated at a single flow rate or over a very narrow band of flow rates. The pump drive motor is connected directly to the battery, and the flow rate is manually adjusted by a restriction in the inlet line. As the battery voltage decreases, the speed of the piston drive motor decreases and the flow rate drops. The restriction must be manually adjusted to restore the air flow rate to its nominal value, but this is effective only over a limited range. The restriction wastes battery power, and the manual adjustment requires frequent observation of an integral flow meter in series with the restriction. The available personal pumps normally operate at relatively high flow rates, on the order of a few liters per minute, and they cannot provide the required exposure of a charcoal tube at their flow rates. If piston drive speeds are reduced to obtain lower flow rates, the valves cease to function properly and the volumetric efficiency deteriorates. Also the frictional torque of the motors used is excessive compared to the load torque, so that an excessively large battery must be used, preventing realization of an adequately small pump for personal use over a period of 8 hours of operation.

In order to reduce the frictional losses in the drive of a piston pump, it is desirable to operate the piston at a relatively low speed. If the pump flow rate is varied by varying the drive speed, then at the low flow rates and low drive speeds cyclic torque variations are very pronounced. If the drive speed is varied by varying the terminal voltage of the drive motor through a rheostat between the power source and the motor, the cyclic torque fluctuations can cause excessive cyclic speed variations, since cyclic current variations can cause appreciable voltage drops across the rheostat, reducing the voltage applied to the motor. An additional drawback in the use of a rheostat between the power supply and the motor is that it is difficult to start the motor at low voltage settings corresponding to low speeds, due to the increased torques caused by static friction and also because of unfavorable mechanical ratios related to the position of the piston.

It is an object of this invention to provide a miniature, battery-operated pump that will provide a uniform, constant flow rate, sufficiently low in magnitude to permit operation with a charcoal tube for a period of eight hours without saturating the charcoal tube.

It is a second object of this invention to provide a pump in which the drive speed can be indicated as a measure of the flow rate and the total motion of the drive can be indicated as a measure of the total volume of air pumped.

It is a third object of this invention to provide a pump driven by a DC motor such that the motor terminal voltage can be indicated as a measure of flow rate and the motor terminal voltage can be electrically integrated to provide an output that is a measure of the total volume of air passed through the pump.

It is another object of this invention to provide a pump driven by a DC motor in which the average fluid flow rate can be maintained at a selectable fixed value by maintaining the motor terminal voltage at a corresponding fixed value.

It is still another object of this invention to provide a pump driven by a DC motor with minimal instantaneous speed variations due to cyclic torque variations of the pump drive and with the capability to start at low values of terminal voltage corresponding to low values of drive speed.

The improved regulated fluid pump meets the previously listed objectives by providing mechanical means to propel the fluid between the inlet and outlet of the housing at an average flow rate which has a substantially linear relation to the average speed of the fluid-propelling means in a flow range between a minimum value and a maximum value of flow rate. The fluid-propelling means is driven by a DC motor with a constant magnetic field and a wound armature that has a characteristic, when connected to the fluid-propelling means, that provides a substantially linear relation between the drive speed and the voltage applied to the armature in a speed range corresponding to the flow range between the minimum and maximum flow rates. Electrical regulating means are included to maintain the voltage applied to the terminals of the motor armature at a selectable fixed value in a voltage range corresponding to the flow range between the minimum and maximum flow rates.

The relation between flow rate and drive speed and the relation between drive speed and motor terminal voltage must be linear within ±5% to meet the requirements for a pump to be used with a sorbent-filled tube. A pump that meets these objectives has been built and satisfactorily tested. The fluid-propelling means is a reciprocating piston sealed by a diaphragm, acting in conjunction with unidirectional inlet and outlet valves. The specified maximum pressure drop at maximum flow rate for a charcoal-filled tube is 2.5 inch of water at 200 cc/min. The minimum flow rate for eight hours of operation is 20 cc/min. The linear flow range is determined by the pressure drop across the valves at the maximum flow rate, and at the minimum flow rate, by the reverse leakage through the valves. Satisfactory linearity was obtained in this flow range with an umbrella-shaped valve made of unreinforced silicone rubber.

The linearity between drive speed and motor terminal voltage was obtained by using a permanent magnet DC motor with a skew-wound armature having a low ratio of friction torque to stalled torque at the maximum terminal voltage connected to a piston with a low friction torque, so that the deviation from the linear voltage speed calibration due to the armature drop is within specified limits.

The electrical regulating means included a semi-conductor amplifier or electronic valve having a relatively fast response compared to the cyclic frequency of the motor to modulate the armature current and maintain the instantaneous terminal voltage constant during cyclic torque variations. The amplifier also supplies the full selected voltage to the motor in the stalled condition, producing a high torque to start the motor.

The features and advantages of the invention will be understood by reference to the following drawings.

In the drawings,

FIG. 1 is a combined schematic diagram and partially sectioned view of the regulated fluid pump.

FIG. 2 is a schematic diagram illustrating the preferred means of electrical regulation of the pump.

FIG. 3 is a schematic diagram illustrating a variation of the electrical regulating means.

FIG. 4 is a schematic diagram illustrating a second variation of the electrical regulating means.

FIG. 5 is a diagram of the speed-torque characteristic of a DC motor with a constant magnetic field, illustrating the performance of the pump drive.

FIG. 6 is a diagram illustrating a skew winding on a DC motor armature.

Referring now to FIG. 1, the regulated fluid pump includes a fluid-filled housing 10, with an inlet 12, and an outlet 14, mechanical means 16, to propel the fluid between the inlet and the outlet, a DC motor 18 with a constant magnetic field and a wound armature with electrical terminals connected to drive the fluid propelling means, a source of DC electrical power 20, and electrical regulating means 22 connecting the DC source with the DC motor and regulating the voltage applied to the terminals of the motor armature at a selectable fixed value.

The pump housing 10 is an assembly of an inlet housing 24 identical valve plates 26 and 28, and pump body 30.

The fluid propelling means 16 includes a piston 32, a unidirectional valve 34 between the housing inlet 12 and the piston, permitting free flow of fluid from the inlet to the piston, and a unidirectional valve 36, permitting free flow of fluid from the piston through the outlet. The propelled fluid is prevented from leaking past the piston by a diaphragm seal 38 which is clamped between the pump body 30 and a pump and drive base 40. Piston 32 is driven by a crank consisting of a crankpin 42 connected between throw arms 44 and 46 which are held in bearings 48 and 50 mounted in base 40.

Throw arm 44 is rotated by motor 18 through a reduction gear transmission 52, applying reciprocating motion to the piston through the crankpin 42. Throw arm 46, which rotates with throw arm 44 and crankpin 42, is connected to a mechanical counter 54, which indicates accumulated motion of the piston as a measure of the total volume of fluid passed through the pump.

The application of the pump in drawing fluid through a collector of pollutants, is illustrated by sorbent-filled filter tube 56, which is connected to the housing inlet through a rigid tube 58 sealed by O-ring 60.

The DC source as shown in FIG. 1, includes a power supply 62 which delivers DC power to the motor through the electrical regulating means 22, and a voltage supply which delivers a variable DC reference voltage to the electrical regulating means through terminal 64. The variable reference voltage supply shown in FIG. 1, is a potentiometer 66, connected across the terminals of the power supply 62, which is shown as a battery. The function of the electrical regulating means is to modulate the DC current fed from the power supply to the motor so as to maintain the motor terminal voltage $E_T$ in a given relationship to the reference voltage $E_R$. A voltmeter 68 connected across the motor terminals, indicates the regulated voltage as a measure of the flow rate through the pump due to the linear relationship between flow rate and drive speed and the linear relationship between drive speed and motor terminal voltage, which is a specified requirement for the improved fluid pump. As an alternative to the use of a voltmeter to indicate motor terminal voltage as a measure of flow rate, potentiometer 66 can be supplied with a scale 70 calibrated in units of motor terminal voltage, or units of flow rate.

The preferred embodiment of the DC power source and the electrical regulating means, is shown in FIG. 2. Here the DC power supply is a battery 72. The DC reference voltage supply consists of a second battery 74 connected through a resistor 76 to a voltage selecting potentiometer 78. The electrical regulating means includes an electronic amplifier 80 whose input is connected to the voltage reference supply and whose output is connected to the motor. In FIG. 2, the amplifier includes two transistor stages in which the emitter of the first stage is connected to the base of the second stage, the collectors of the two stages are connected to the DC power supply, the emitter of the second stage is connected to the motor armature, and the base of the first stage is connected to the wiper arm of potentiometer 78. The transistors are connected in the familiar Darlington configuration, together with the motor armature winding, as an emitter follower. On-off switch 82 simultaneously connects the power supply and the voltage reference supply to the circuit.

The transistorized emitter-follower in the Darlington connection 80 is desirable for two reasons. First, when operated at saturation there is a minimum drop of 0.5 to 0.7 volts across the second stage, which does not seriously increase the voltage in the power supply required to drive the DC motor. Thus, a minimum number of cells is required for a power battery, with the attendant advantages such as intrinsic safety of operation. The second advantage is in the very high gain that is achieved in amplifier 80, typically of the order of 10,000 or more, thus minimizing the current drain from the reference voltage supply. For a typical current from the power battery 72 to the motor of 40 milliamperes, a voltage of the reference battery 74 of 4 volts, and a resistance for potentiometer 78 of 100,000 ohms, the current through the potentiometer is 40 microamperes and that through the amplifier is 5 microamperes, so that the capacity and size of the reference battery 74 can be kept to a minimum.

In order to obtain the least voltage drop across the diodes of the second stage of amplifier 80, it has been found desirable to utilize a higher maximum voltage from the voltage reference supply to drive the base of the first stage, than the voltage from the power supply to the collectors of the two stages. Since the smallest increment by which the voltage of the reference voltage supply can be higher than that of the power supply is the voltage of a single battery cell, the maximum voltage of battery 74 can be excessive, and this can cause a reverse current flow through the base of the first stage. For this reason, dropping resistor 76 is used, so that when the wiper arm of potentiometer 78 is at its extreme or high voltage position, the voltage supply to the base of the first stage will be below that value which will cause a reversed current. It has been found that where the amplifier is made of silicon transistors, where the power supply consists of two nickel cadmium cells with a maximum voltage of approximately 2.5 volts, and where the reference supply battery 74 is composed of three mercury cells with a total voltage of approximately 4 volts, that the value of resistor 76 can be from 6 to 10 percent of the resistance of potentiometer 78 before significant reverse current flow will occur.

Because of the linear relation between fluid flow rate and drive speed, and the linear relation between drive speed and motor terminal voltage, it is possible to use an electrical totalizer rather than the mechanical counter 54 to indicate the total volume of fluid passed through the pump. Such a totalizer is illustrated by electrical integrator 84, which integrates the motor terminal voltage, which is proportional to the flow rate. One type of integrator that can be used is shown as a familiar operational amplifier with a high gain amplifier 86, an input resistor 88 and a feedback capacitor 90. The total volume of fluid passed through the pump is the time integral of the flow rate. The voltage output $E_V$ of integrator 84 is a time integral of the motor terminal voltage $E_T$. Because the motor terminal voltage is linearly related to the flow rate, voltage $E_V$ is proportional to the total volume of fluid passed through the pump.

A variation of the electrical regulating means is illustrated in FIG. 3. Here, the electronic amplifier is an operational amplifier with a high gain amplifier 92, an input resistor 94, and a feedback resistor 96. The wiper arm of the potentiometer 98 feeds a reference voltage $E_R$ to resistor 94. The output voltage $E_T$, which is fed to the terminals of the pump drive motor 18, is directly proportional to the reference voltage.

A second variation of the electrical regulating means is illustrated in FIG. 4. In this embodiment the electronic amplifier is a high gain differential amplifier 100 with two inputs. The reference voltage $E_R$ is fed to one of the inputs from the wiper arm of potentiometer 102. The output voltage $E_T$, applied to the terminals of motor 18, is fed back to the second input of the differential amplifier. Because of the high gain of the amplifier, the terminal voltage $E_T$ is substantially equal to the reference voltage $E_R$.

The volumetric efficiency of the pump, and therefore the linearity between flow rate and drive speed, is determined by the characteristics of the unidirectional valves 34 and 36. The volumetric efficiency will be adversely affected as the forward resistance of the valves increases and as leakage in the reverse direction increases. For a compressible fluid such as air, the volumetric efficiency is also affected by the resistance of the sorbent-filled filter tube 56, so that it is of even more importance that the unidirectional valves have a low forward pressure drop. The valves used in the sampler pump that was built and tested were umbrella-shaped valves, as illustrated in FIG. 1, molded of unreinforced silicone rubber with a lip thickness of 0.010/0.015 inch. These valves have a forward pressure drop of less than 0.75 inch of water at an air flow rate of 200 cc/min. The reverse leakage was significantly less than 5 cc/min at a reverse pressure drop of less than 0.1 inch of water. Ball valves and flapper valves were also tested, some having resistances as high as 3.5 inch of water at 200 cc/min and reverse flows as high as 100 cc/min at 1 inch of water. Tests of the pump with the umbrella-type valves showed satisfactory linearity in a range between 20 cc/min and 200 cc/min.

The linearity of drive speed to terminal motor voltage is determined by the resistance of the piston drive elements, which applies a load torque to the motor, and the no-load frictional torque of the motor. Since the effect of increased torque is to draw increased current through the motor armature, there is an increased resistive voltage drop across the armature that bucks the applied voltage and reduces the speed. This is illustrated in FIG. 5 and also by the equation, $$n = n_s \left[ E_T - I_S R_A \left( \frac{T_T}{T_S} \right) \right]$$

where $n$ is the actual speed; $n_s$ is the specific speed, rpm per volt, which is determined by the geometry and field strength of the motor; $E_T$ is the terminal voltage; $I_S$ is the armature current at stall; $R_A$ is the armature resistance; $T_T$ is the total torque; $T_S$ is the stalled torque. It is evident from the equation that if the total torque is zero, then the speed is directly proportional only to the motor terminal voltage. If the torque equals the stalled torque, then the speed is equal to zero, and the stalled current multiplied by the armature resistance equals the terminal voltage. It is seen, then, that the linearity is determined primarily by the ratio of the total torque applied to the drive motor, to the stalled torque of the motor. To meet the accuracy requirements specified for air flow measurement through sorbent-filled tubes, the total torque $T_T$ applied to the motor armature should be equal to or less than 10% of the stalled motor torque $T_S$ at the maximum value of motor terminal voltage $E_T$ max. This is a limiting case when the deviation from linearity of the flow rate/drive speed characteristic is negligible.

The motor used in the pump that has been built and tested is of the well-known Faulhaber design, in which the motor armature has a skew winding such that the torque-producing conductors are positioned at an angle greater than zero to the axis of the armature. This configuration is illustrated in FIG. 6. Tests of the pump with the arrangement described in FIG. 1, in which the effective area of the piston is 0.37 square inches, the drive motor 18 is of the Faulhaber type 050/015, and the reduction gear 52 has a ratio of 41 to 1, showed that the ratio of total torque to the no-load frictional torque of the motor was a maximum of 2 or less. With a limiting case where total torque $T_T$ is equal to or less than 10% of the stalled motor torque $T_S$, the limiting value of the no-load friction torque of the motor $T_F$ has a maximum ratio to the stalled torque of 1 to 20. These values are specified as being the maximum values of total torque and friction torque that can be tolerated to achieve the required linearity to provide indications of flow rates and total air volume passed through a sorbent-filled filter with the required accuracy.

Permanent magnet DC motors with the required low ratio of friction torque to stalled torque, which could also be expressed as a ratio of no-load current to stalled current, are not generally available. Due to certain characteristics of the skew winding, the idle-running friction torque is reduced and motor efficiency increased. The following table illustrates the variation in the characteristic friction torque to stalled torque ratios (no-load current to stalled current).

| Motor Type | Friction Torque / Stalled Torque or { No Load Current / Stalled Current } |
|---|---|
| Faulhaber 050/010 - 2 Volts | .036 |
| Faulhaber 050/015 - 1.5 Volts | .027 |
| Globe HM - 6 Volts | .081 |
| Globe MM - 4 Volts | .072 |
| Globe SS - 6 Volts | .11 |
| Globe SD - 6 Volts | .10 |

It is evident that only the first two motors listed would be useable to provide the required linearity, and therefore accuracy, of the pump.

With the components described above for the pump that has been tested, it was found that the linearity between flow rate and motor terminal voltage, as well as the linearity between flow rate and drive speed, was accurate within ± 5%. If the torque characteristics of the fluid-propelling means and of the drive motor were not maintained within a range providing a tolerable linear calibration, then it would not be possible to regulate the drive speed by regulating the motor terminal voltage, but some other means would be required, such as use of a tachometer generator to directly sense the drive speed. Also, it would not be possible to supply a single calibration factor with a pump that could be applied to the motor terminal voltage as a measure of flow rate, nor could the motor terminal voltage be integrated to provide a measure of total fluid volume.

While the invention has been described in its preferred embodiments, it is to be understood that the words which have been used are words of description rather than of limitation and that changes within the purview of the appended claims may be made without departing from the true scope and spirit of the invention in its broader aspects.

What is claimed is:

1. A regulated fluid pump including, a fluid-filled housing with an inlet and an outlet, mechanical means to propel the fluid between the inlet and the outlet at an average flow rate which has a substantially linear relation to the average speed of the fluid propelling means in a flow range between a minimum value and a maximum value of flow rate, a DC motor with a constant magnetic field and a wound armature with electrical terminals and an axis, connected to drive the fluid propelling means and terminals and having a characteristic when so connected providing a substantially linear relation between the drive speed and the voltage applied to the armature terminals in a speed range between a minimum value and a maximum value of drive speed corresponding to the minimum and maximum flow rate, a source of DC electrical power, electrical regulating means connecting the DC source with the DC motor and regulating the voltage applied to the terminals of the motor armature of a selectable fixed value between a minimum value and maximum value of voltage corresponding to the minimum and maximum values of drive speed so as to maintain the speed of the fluid propelling means at a corresponding fixed value in the linear speed range of the DC motor and the average fluid flow rate at a corresponding fixed value in the linear flow range of the pump, in which the substantially linear relation between the motor terminal voltage and the drive speed is provided by a fluid propelling means characterized by a mechanical resistance at the maximum drive speed that applies a load torque to the motor armature that is equal to or less than 10 percent of the stalled motor torque at the maximum voltage.

2. A regulated fluid pump of the character claimed in claim 1, with a motor having a maximum ratio of friction torque to the stalled torque at the maximum terminal voltage of 1 to 20.

3. A regulated fluid pump including, a fluid-filled housing with an inlet and an outlet, mechanical means to propel the fluid between the inlet and the outlet at an average flow rate which has a substantially proportional relation to the average speed of the fluid propelling means in a flow range between a minimum and a maximum value of flow rate, a DC motor with a constant magnetic field and a wound armature with electrical terminals and an axis, connected to drive the fluid propelling means and having a characteristic when so connected providing a substantially proportional relation between the drive speed and the voltage applied to the armature terminals in a speed range between a minimum value and a maximum value of drive speed corresponding to the minimum and maximum flow rates, a source of DC electrical power, electrical regulating means connecting the DC source with the DC motor and regulating the voltage applied to the terminals of the motor armature at a selectable fixed value between a minimum value and a maximum value of voltage corresponding to the minimum and maximum values of drive speed so as to maintain the speed of the fluid propelling means at a corresponding fixed value in the proportional speed range of the DC motor and the average fluid flow rate at a corresponding fixed value in the proportional flow range of the pump, and totalizing means to indicate the total motion of the mechanical fluid propelling means as a measure of the total volume of fluid passed between the inlet and the outlet in which the DC source includes a power supply, which delivers DC power to the motor through the electrical regulating means and a voltage supply, which delivers a selected DC reference voltage to the electrical regulating means.

4. A regulated fluid pump of the character claimed in claim 3, in which the DC reference voltage supply is a potentiometer, connected to a battery.

5. A regulated fluid pump of the character claimed in claim 4, including a resistor between the potentiometer and the battery.

6. A regulated fluid pump of the character claimed in claim 3, in which the electrical regulating means includes an electronic amplifier, whose input is connected to the voltage reference supply and whose output is connected to the motor.

7. A regulated fluid pump of the character claimed in claim 6, in which the amplifier is an operational amplifier with an input resistor and a feedback resistor causing the output voltage to be directly proportional to the reference voltage applied to the input.

8. A regulated fluid pump of the character claimed in claim 6, in which the amplifier is a differential amplifier with two inputs, one input connected to the voltage reference supply, and the other input connected to the output of the amplifier.

9. A regulated fluid pump of the character claimed in claim 6, in which the amplifier includes two transistor stages in which the emitter of the first stage is connected to the base of the second stage, the collectors of the two stages are connected to the DC power supply, the emitter of the second stage is connected to the motor armature, and the base of the first stage is connected to the reference voltage supply.

10. A regulated fluid pump of the character claimed in claim 4, in which the voltage indicating means is a calibrated scale on the potentiometer.

11. A regulated fluid pump including, a fluid-filled housing with an inlet and an outlet, mechanical means to propel the fluid between the inlet and the outlet at an average flow rate which has a substantially proportional relation to the average speed of the fluid propelling means in a flow range between a minimum and a maximum value of flow rate, a DC motor with a constant magnetic field and a wound armature with electrical terminals and an axis, connected to drive the fluid propelling means and having a characteristic when so connected providing a substantially proportional relation between the drive speed and the voltage applied to the armature terminals in a speed range between a minimum value and a maximum value of drive speed corresponding to the minimum and maximum flow rates, a source of DC electrical power, electrical regulating means connecting the DC source with the DC motor and regulating the voltage applied to the terminals of the motor armature at a selectable fixed value between a minimum value and a maximum value of voltage corresponding to the minimum and maximum values of drive speed so as to maintain the speed of the fluid propelling means at a corresponding fixed value in the proportional speed range of the DC motor and the average fluid flow rate at a corresponding fixed value in the proportional flow range of the pump, and totalizing means to indicate the total motion of the mechanical fluid propelling means as a measure of the total volume of fluid passed between the inlet and the outlet, in which the totalizing means is an electronic integrator with an input connected to a terminal of the motor armature and providing a voltage at its output, which is an integral of the motor terminal voltage as a measure of the total volume of fluid passed through the pump.

12. A system for providing a flow of fluid which can be linearly calibrated and controlled, comprising:

a fluid pump including mechanical means to propel the fluid, in which the average fluid flow rate is linearly related to the average speed of the mechanical fluid propelling means over a predetermined flow range;

a DC electric motor connected to drive said fluid propelling means, the drive speed being linearly related to the DC voltage applied to the motor over a predetermined drive speed range corresponding to said predetermined flow range;

means for applying a variable regulated DC voltage to said motor, the value of the voltage being limited to a predetermined range corresponding to said predetermined speed range; and totalizing means to indicate the total motion of the mechanical fluid propelling means as a measure of the total volume of fluid pumped over the linear flow range;

wherein said motor has a stalled torque at the maximum value of DC voltage in said predetermined voltage range that is at least ten times the maximum torque required to drive said mechanical fluid propelling means within the predetermined flow range.

13. The system of claim 12 wherein said DC motor has a maximum ratio of friction torque to the stalled torque at the maximum value of applied DC voltage of five percent.

14. The system of claim 12 wherein said DC motor includes a permanent magnet for producing a constant magnetic field.

15. The system of claim 12 wherein said pump comprises:

a housing having an inlet and an outlet adapted to receive and discharge fluid, respectively;

a piston disposed within said housing;

a first unidirectional valve between the inlet and the piston permitting free flow of fluid from the inlet to the piston;

a second unidirectional valve between the piston and the outlet permitting free flow of fluid from the piston to the outlet; and, a crankshaft connecting said piston to said DC motor.

16. The system of claim 12 further including a sorbent-filled filter connected to the housing inlet.

17. The system of claim 12 wherein said regulated DC voltage applying means comprises:
a DC power source;
a DC reference supply; and
an electronic amplifier connected between said power source and said motor, and having its input connected to said reference supply.

18. The system of claim 17 wherein said DC reference supply comprises a potentiometer connected in parallel with said power source.

19. The system of claim 17 wherein said DC reference supply comprises a battery, and a potentiometer connected across said battery.

20. The system of claim 19 wherein said potentiometer includes a wiper arm and a scale calibrated in units of flow rate operatively associated therewith.

21. The system of claim 17 wherein said electronic amplifier comprises a transistorized emitter-follower in a Darlington configuration with its input connected to said reference supply and its output connected to said motor armature.

22. The system of claim 12 further including an electronic integrator connected to receive the motor terminal voltage at its input.

23. The system of claim 22 wherein said electronic integrator comprises an operational amplifier, the output of which is indicative of the total volume of fluid which has passed through said pump in a particular time interval.

24. The system of claim 17 wherein said electronic amplifier comprises an operational amplifier.

25. The system of claim 17 wherein said electronic amplifier comprises a differential amplifier having one input connected to said reference and the second input connected by a feedback path to its output.

26. A system for providing a flow of fluid which can be linearly calibrated and controlled, comprising:
a fluid pump in which the average fluid flow rate is linearly related to the average fluid propelling means speed over a predetermined flow range;
a DC electric motor connected to drive said fluid propelling means, the drive speed being linearly related to the DC voltage applied to the motor over a predetermined drive speed range corresponding to said predetermined flow range; and
means for applying a variable regulated DC voltage to said motor, the value of the voltage being limited to a predetermined range corresponding to said predetermined speed range,
wherein said DC motor has a maximum ratio of friction torque to the stalled torque at the maximum value of applied DC voltage of five percent.

27. A regulated fluid pump of the character claimed in claim 3 including means to indicate the motor terminal voltage as a measure of flow rate.

28. A regulated fluid pump of the character claimed in claim 1 including totalizing means to indicate the accumulated motion of the fluid propelling means as a measure of the total volume of fluid passed between the inlet and the outlet.

29. A regulated fluid pump of the character claimed in claim 28 in which the totalizing means is a mechanical counter connected to the motor.

30. A regulated fluid pump including a fluid-filled housing with an inlet and an outlet, mechanical means to propel the fluid between the inlet and the outlet at an average flow rate which has a substantially linear relation to the average speed of the fluid propelling means in a flow range between a minimum value and a maximum value of flow rate,
a DC motor with a constant magnetic field and a wound armature with electrical terminals and an axis, connected to drive the fluid propelling means and having a characteristic when so connected providing a substantially linear relation between the drive speed and the voltage applied to the armature terminals in a speed range between the minimum value and a maximum value of drive speed corresponding to the minimum and maximum flow rates,
a source of DC electrical power,
electrical regulating means connecting the DC source with the DC motor and regulating the voltage applied to the terminals of the motor armature at a selectable fixed value between a minimum value and maximum value of voltage corresponding to the minimum and maximum values of drive speed so as to maintain the speed of the fluid propelling means at a corresponding fixed value in the linear speed range of the DC motor and the average fluid flow rate at a corresponding fixed value in the linear flow range of the pump,
in which the substantially linear relation between the motor terminal voltage and the drive speed is provided by means comprising a motor having a maximum ratio of friction torque to the stalled torque at the maximum terminal voltage of 1 to 20.

* * * * *